United States Patent [19]

Tanji et al.

[11] Patent Number: 5,601,546
[45] Date of Patent: Feb. 11, 1997

[54] DISPOSABLE DIAPER

[75] Inventors: Hiroyuki Tanji; Makoto Suekane, both of Ehime-ken, Japan

[73] Assignee: Uni-Charm Corporation, Ehime-ken, Japan

[21] Appl. No.: 408,260

[22] Filed: Mar. 21, 1995

[30]     Foreign Application Priority Data

Mar. 24, 1994   [JP]   Japan ................................. 6-053632

[51] Int. Cl.$^6$ ..................................................... A61F 13/15
[52] U.S. Cl. ...................................... 604/385.2; 604/385.1
[58] Field of Search .................. 604/358, 385.1, 604/385.2

[56]              References Cited

U.S. PATENT DOCUMENTS

| 4,662,877 | 5/1987 | Williams | 604/385.2 |
| 4,704,116 | 11/1987 | Enloe | 604/385.2 |
| 5,021,051 | 6/1991 | Hiuke . | |
| 5,167,653 | 12/1992 | Igaue et al. | 604/385.2 |

FOREIGN PATENT DOCUMENTS

93/09739   5/1993   WIPO ................................ 604/385.2

*Primary Examiner*—Robert A. H. Clarke
*Attorney, Agent, or Firm*—Lowe, Price, LeBlanc & Becker

[57]               ABSTRACT

A disposable diaper is provided with a pair of elastic crotch zone cuffs extending in parallel to each other longitudinally across a front zone, a crotch zone and a rear zone, said cuffs each being bonded along a base thereof as well as at portion of longitudinally opposite end thereof and in proximity thereof base to a topsheet inside transversely opposite side edges of a liquid-absorbent core sandwiched between a topsheet and a backsheet so as to be collapsed inwardly of said diaper and have free side edges thereof folded outwardly onto non-folded portions of the cuffs which have already been collapsed, and longitudinally opposite ends of said free side edges being bonded to the cuffs or to the topsheet.

2 Claims, 4 Drawing Sheets

DISPOSABLE DIAPER

BACKGROUND OF THE INVENTION

The present invention relates to a disposable diaper and particularly to a disposable diaper with elasticized leg cuffs.

It is well known in this field of technique to provide disposable diapers with a pair of cuffs longitudinally extending in parallel to each other and having a tendency to be stood up toward the user's crotch in order that leakage of excretion which otherwise would possibly occur can be effectively avoided. For example, U.S. Pat. No. 5,021,051 discloses the technique according to which longitudinally opposite ends of such cuffs collapsed inwardly of a diaper are bonded to a topsheet and, in a crotch zone of the diaper, free side edges of the cuffs are folded outwardly of the diaper with opposed outer surface sections of the same cuff put one on another and partially bonded together so that a relatively wide space may be obtained between the free side edges of the respective cuffs in the crotch zone of the diaper. In this manner, there is no apprehension that unacceptably large area of the topsheet might be covered by the collapsed cuffs in the crotch zone and consequently the effective area of the topsheet for liquid permeation might be significantly reduced even though the cuffs are dimensioned to be relatively wide in order that relatively high barriers may be formed by the cuffs when they are stood up.

For the disposable diaper generally dealing with loose passage of high fluidity, the pair of cuffs having the tendency to be reacted toward the user's crotch may be arranged to define a relatively small space between their base and thereby to effectively restrain a spread of loose passage and therefore to minimize an area of the user's skin possibly stained with loose passage. Additionally, by dimensioning the cuffs to have relatively large width and to form relatively high barriers when they are reacted, leakage of loose passage can be reliably avoided even if the diaper is considerably spaced from the user's crotch, since the cuffs will satisfactorily function as barriers. However, reducing the space between the base of the respective cuffs and dimensioning the cuffs to be relatively wide will be accompanied with a problem that the cuffs may cover unacceptably large area of the topsheet, thus substantially reducing the effective area of the topsheet for liquid permeation and seriously preventing the excretion from being properly absorbed. While the technique disclosed in U.S. Pat. No. 5,021,051 should have been developed to solve this problem, it is really difficult for this technique to achieve the desired end, since the free side edges folded in two of the respective cuffs are bonded together in the crotch zone and consequently the cuffs can not form the desired high barriers.

SUMMARY OF THE INVENTION

In view of the problem as mentioned above, it is a principal object of the invention to solve this problem by outwardly folding the free side edges of the respective cuffs having already been collapsed inwardly of the diaper and bonding longitudinally opposite ends of the respective cuffs thus folded to the cuffs themselves or to the topsheet.

The object set forth above is achieved, according to the invention, by a disposable diaper comprising a liquid-permeable topsheet, a liquid-impermeable backsheet and a liquid-absorbent core sandwiched between these two sheets, these components being assembly together so as to form a front zone, a rear zone and a crotch zone extending between said front and rear zones, and further comprising a pair of cuffs extending in parallel to each other longitudinally across said front and rear zones as well as said crotch zone, each of said cuffs having a base, an elastic free side edge extending in parallel to said base and longitudinally opposite ends, and these cuffs being bonded along said base and at said longitudinally opposite ends to said topsheet so that said free side edges have a tendency in said crotch zone to be stood up from said topsheet toward the user's crotch, wherein said cuffs are bonded along said base as well as at portions of said longitudinally opposite ends in the proximity of said base to said topsheet inside transversely opposite side edges of said liquid-absorbent core so as to be collapsed inwardly of said diaper and folded along said free side edges outwardly of said diaper onto non-folded portions of the collapsed cuffs; and longitudinally opposite ends of said free side edges are bonded to said non-folded portions or to the topsheet.

With such arrangement, the base of the cuffs are bonded to the topsheet inside the transversely opposite side edges of the liquid-absorbent core in order that the space between the base of the respective cuffs can be reduced. The free side edges of the respective cuffs having already been collapsed inwardly of the diaper are then folded outwardly of the diaper and bonded at their longitudinally opposite ends to the topsheet so that the cuffs do not cover unacceptably large area of the topsheet and may form the desired high barriers when they are stood up.

BRIEF DESCRIPTION OF THE DRAWINGS

A disposable diaper according to the invention will be described in more detail with respect to the accompanying drawings, in which.

PREFERRED EMBODIMENTS OF THE INVENTION

Figure 1:
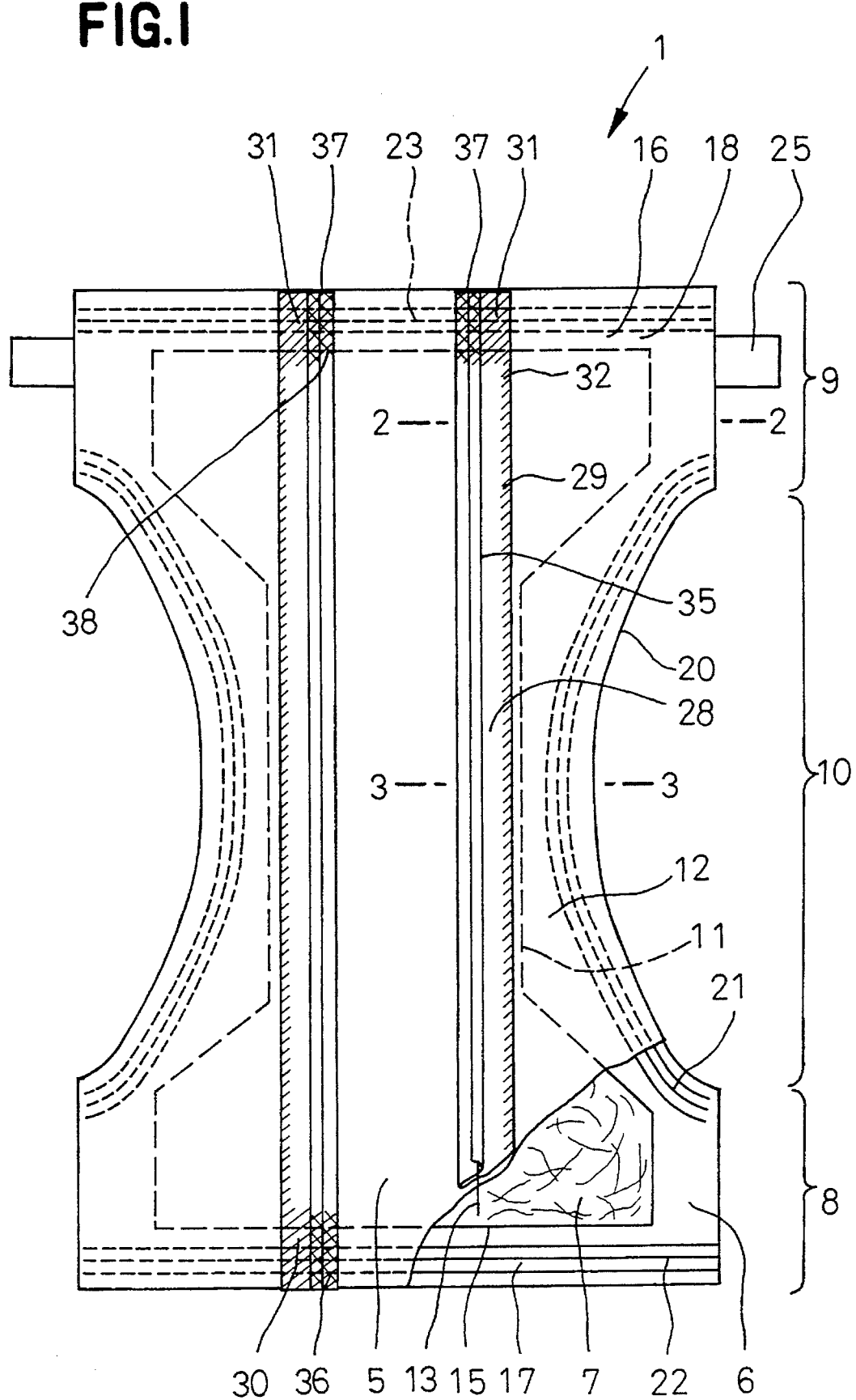
FIG. 1 is a plan view of a diaper as partially broken away.

Referring to FIG. 1, a diaper 1 comprises a liquid-permeable topsheet 5, a liquid-impermeable backsheet 6 and a liquid-absorbent core 7 sandwiched between these two sheets 5, 6. These components 5, 6, 7 are assembled together so as to form a front zone 8, a rear zone 9 and a crotch zone 10 extending between these zones 8, 9. Portions of the top- and backsheets 5, 6 extending outward from transversely opposite side edges of the liquid-absorbent core 7 are bonded together to define first cuffs 12 destined to surround respective legs and portions of the top- and backsheets 5, 6 extending outward from longitudinally opposite edges 15, 16 of the liquid-absorbent core 7 define longitudinally opposite ends 17, 18 of the front and rear zones 8, 9, respectively. The first cuffs 12 have notches 20 destined to define respective leg-openings and elastic members 21 are bonded under stretched condition to the respective first cuffs 12 along the notches 20 for fitness around the respective legs. Elastic members 22, 23 and bonded under transversely stretched condition to the ends 17, 18 for fitness around the waist. Tape fasteners 25 extend outward from transversely opposite side edges of the rear zone 9.

In the diaper 1, a pair of narrow second cuffs 28 for the crotch zone extend in parallel to each other longitudinally across the front and rear zones 8, 9. The second cuffs 28 have their base or outer side edges 29 bonded to the topsheet 5 at location inside the respective side edges 11 of the liquid-absorbent core 7 so as to be collapsed inwardly of the diaper 1 and have portions of their longitudinally opposite ends 30, 31 adjacent the respective base or outer side edges 29 also bonded to the topsheet 5. Oblique lines 32 extending left-and-downward indicate the portions of the second cuffs 28 bonded to the topsheet 5. The second cuffs 28 have their free side edges 35 extending in parallel to the base or outer side edges 29 and folded back outwardly of the diaper 1, as will be described later in reference with FIGS. 2 and 3. Longitudinally opposite ends 36, 37 of the respective free side edges 35 are bonded to the portions of the second cuffs 28 which have already been collapsed but not folded, as indicated by oblique lines 38 extending right-and-downward. Elastic members 13 are bonded under their longitudinally stretched condition to the respective free side edges 35 so as to extend between the opposite ends 36, 37 of the respective free side edges 35, and the respective free side edges 35 of the second cuffs 28 are folded back by narrow extents thereof to cover the respective elastic members 13.

Figure 2:
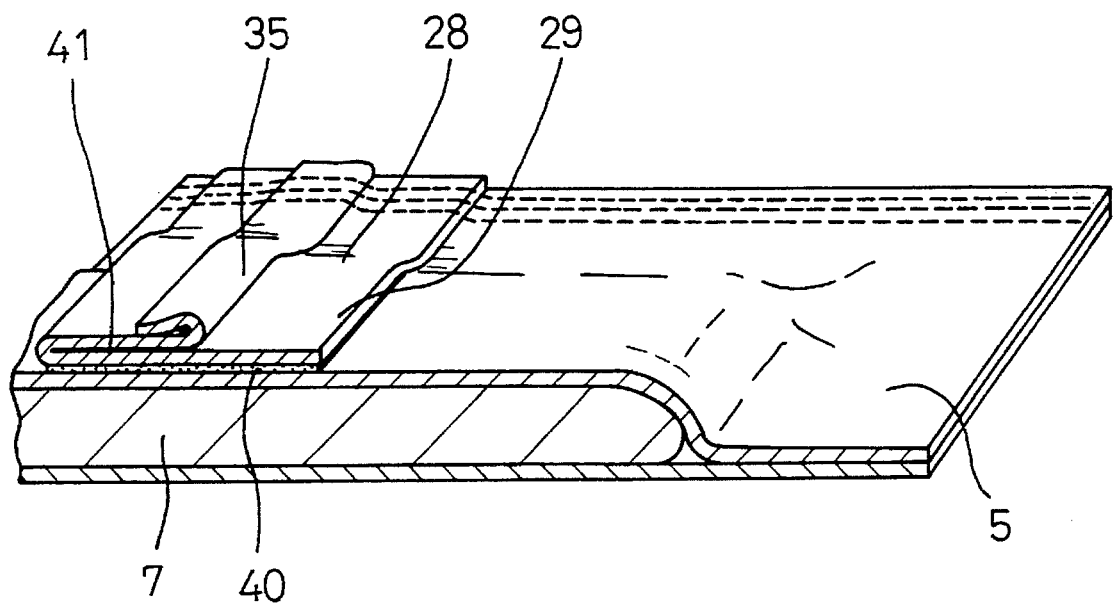
FIG. 2 is a partial perspective view of the diaper as taken along a line 2—2 in FIG. 1.

Referring to FIG. 2, the second cuff 28 is bonded along its base or outer side edge 29 and in the proximity thereof to the upper surface of the topsheet 5 by hot melt adhesive 40, then the free side edges 35 and a portion in proximity thereof are folded outwardly of the diaper 1 and bonded to the already collapsed second cuff 28 by hot melt adhesive 41.

Figure 3:
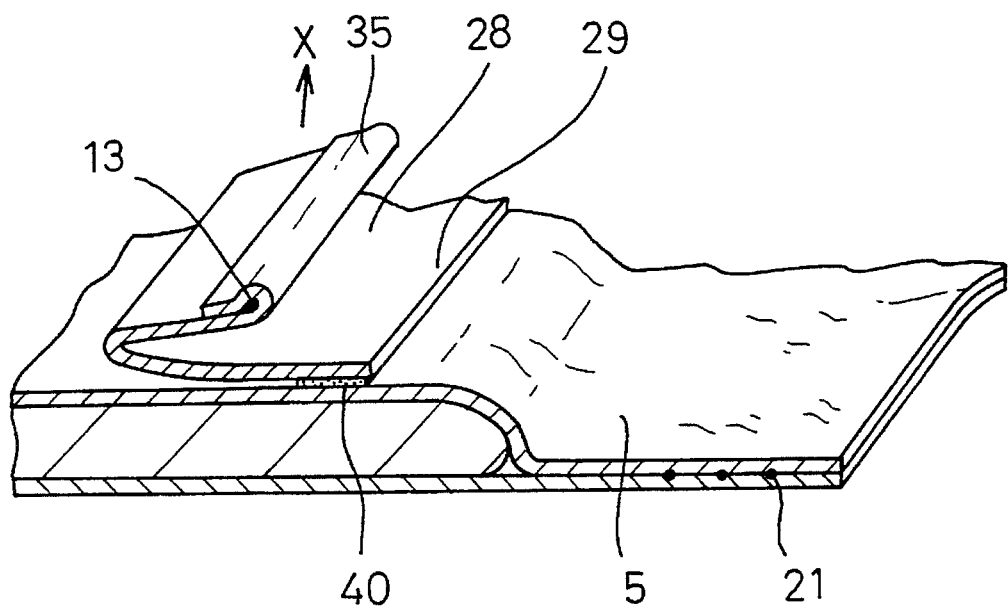
FIG. 3 is a partial perspective view of the diaper as taken along a line 3—3 in FIG. 1.

Referring to FIG. 3, each second cuff 28 has its base or outer side edge 29 bonded to the topsheet 5 and the free side edge 35 and a portion in the proximity thereof folded outwardly of the diaper 1. The second cuff 28 transversely extending from the base or outer side edge 29 to the free side edge 35 includes a zone which is left not bonded to the topsheet 5 and defines a longitudinally narrow portion of the second cuff 28. This narrow portion normally tends to be stood up in a direction indicated by an arrow X, i.e., to be stood up from the upper surface of the topsheet 5 under the contracting effect of the elastic member 13.

Figure 4:
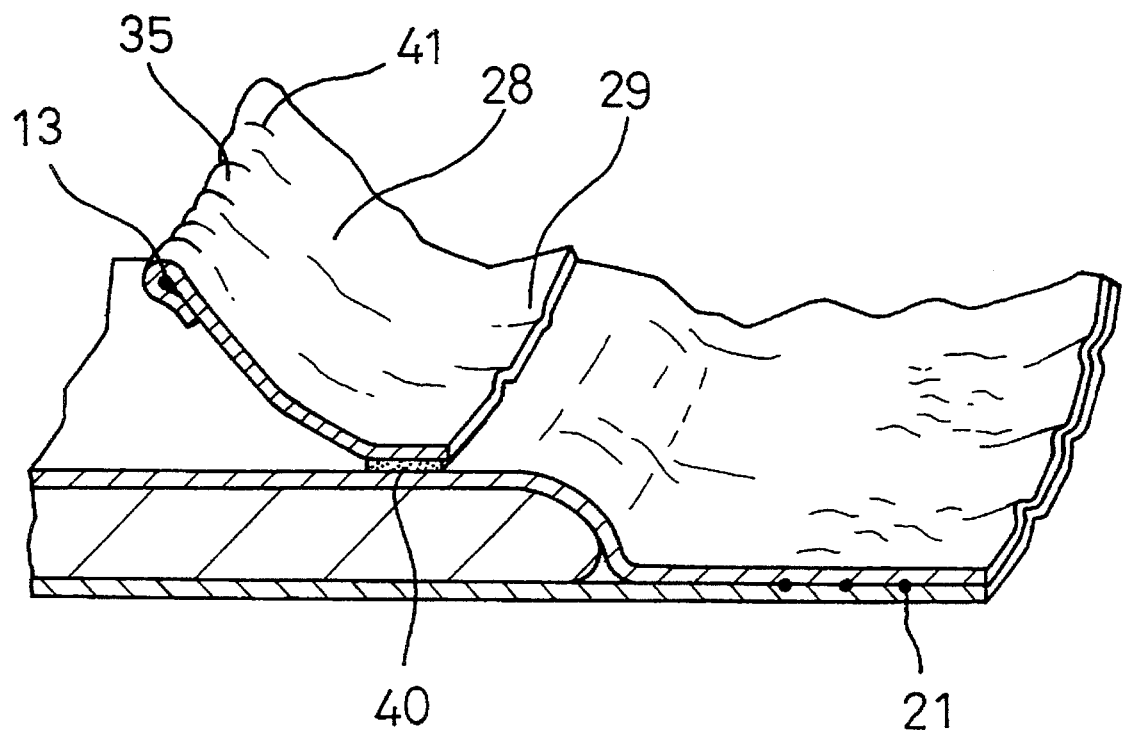
FIG. 4 is a view similar to FIG. 3.

Referring to FIG. 4, such condition is substantially the same as the condition appearing when the diaper 1 is worn. Specifically, as the elastic member 13 contracts between said longitudinally opposite ends of the free side edges 35, the second cuff 28 is stood up from the upper surface of the topsheet 5 on its base or outer side edge 29 so that the free side edge 35 may form a plurality of gathers 41 and bear against the user's crotch (not shown). The stood up second cuff 28 functions as a barrier against excretion of high fluidity such as loose passage and the effectiveness of the second cuff 28 as the barrier becomes further reliable when the free side edge 35 bears against the user's crotch. With the diaper 1 worn, it is well known that a plurality of gathers are formed in said longitudinally opposite ends 17, 18 of the front and rear zones as well as the first cuffs 12 and closely fit around the waist and the legs of the user, respectively, and therefore such aspect will not be described here.

Referring to FIGS. 1 through 4, the free side edges 35 of the collapsed second cuffs 28 are folded outwardly of the diaper 1 to assure the second cuffs 28 to present their width larger than the case in which the second cuffs 28 have no folded portions. Folding of the second cuffs 28 is effective to avoid an apprehension that the second cuffs 28 might cover unacceptably large area of the topsheet 5 even when the base or outer side edges 29 of the second cuffs 28 are located inside the transversely opposite side edges 11 of the liquid-absorbent core 7. Additionally, even if the second cuffs 28 remain collapsed with the diaper 1 worn, the area of the topsheet 5 available for liquid permeation is never reduced due thereto. In other words, if width of each second cuff 28 is dimensioned to form the high barrier when the second cuff 28 is stood up, this will never interfere with function of the topsheet 5. Furthermore, if a large gap is formed between the user's crotch and the diaper 1, the correspondingly wide second cuffs 28 form adequately wide barriers across such large gap.

Figure 5:
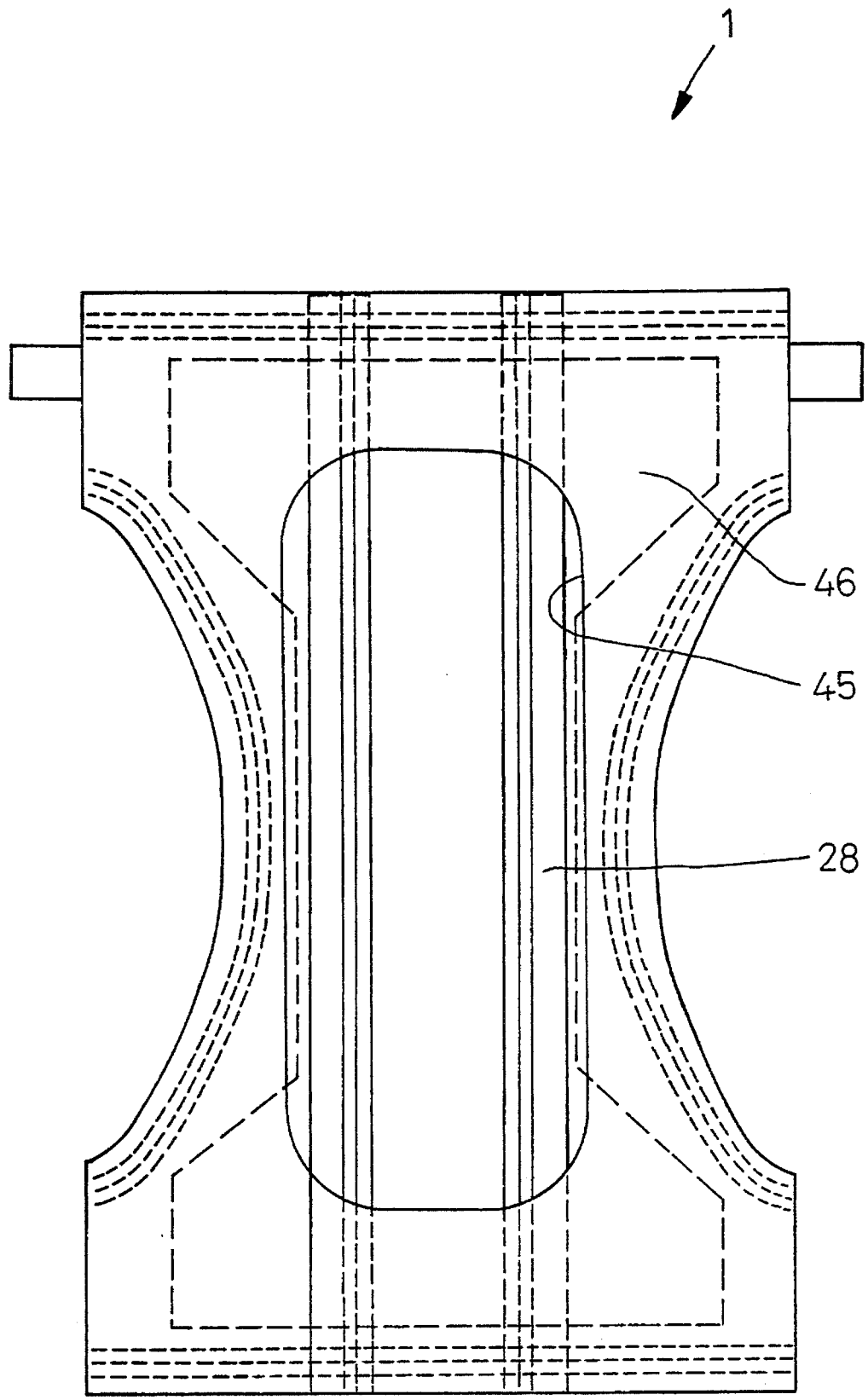
FIG. 5 is a plan view exemplarily showing a specific embodiment of the invention.

Referring to FIG. 5, a liquid-permeable or impermeable cover sheet 46 centrally formed with a longitudinally long circular opening 45 and having the substantially same external shape as the diaper 1 is laid on the diaper 1, partially covering the second cuffs 28. The cover sheet 46 is bonded at least along its outer periphery and the peripheral edge of the opening 45 to the topsheet 5 and the second cuffs 28 by hot melt adhesive (not shown). The opening 45 has a width in said crotch zone 10 larger than the distance between the base or outer side edges 29 of the respective second cuffs 28 so that the second cuffs 28 can be stood up inside the opening 45. In this manner, it is also possible to bond the base or outer side edges 29 as well as the free side edges 35 thereof to the topsheet 5 by utilizing the cover sheet 46 laid on the second cuffs 28.

According to the invention, the second cuffs 28 may be formed by a liquid-permeable or liquid-impermeable or air-impermeable nonwoven fabric or a plastic film and the other members may be formed by respective materials usually used in this field of technique. To bond the various members together, in addition to the well known adhesive or gluing agent, the well known welding technique may be also employed.

It should be noted here, though not shown, that the disposable diaper according to the invention may be in the form of briefs type or short pants type that lateral side edges of the front and rear zones 8, 9 are integrally bonded to each other without employing tape fasteners 25.

With the disposable diaper according to the invention, the respective cuffs for the crotch zone have their base or outer side edges bonded to the topsheet inside the transversely opposite side edges of the liquid-absorbent core and their free side edges folded outward, so it is possible to reduce the distance between the base or outer side edges of the respective cuffs sufficiently to restrain a spread of high fluidity excretion such as loose passage and thereby to limit the area of the user's skin possibly stained with such excretion. These cuffs for the crotch zone can be stood up under the contacting effect of the associated elastic members and there can be dimensioned to have relatively large width without apprehension that these cuffs might cover the topsheet over unacceptably large area and reduce the effective area of the topsheet for liquid permeation.

Except the region defined by the opening of the cover sheet, the base or outer side edges as well as the longitudinally opposite ends of the cuffs bonded to the topsheet are covered by the cover sheet. This feature not only contributes to the improvement of diaper's external appearance but also softens the touch of those bonded portions when they come in contact with the user's skin.

What is claimed is:

1. A disposable diaper comprising:

a liquid-permeable topsheet;

a liquid-impermeable backsheet;

a liquid-absorbent core sandwiched between said topsheet and said backsheet;

said topsheet, said backsheet and said core assembled together so as to form a front zone, a rear zone and a crotch zone extending between said front zone and said rear zone;

a pair of cuffs extending longitudinally and generally parallel to each other along said front zone, said rear zone and said crotch zone;

each of said cuffs having a base side edge and an elastic free side edge extending generally parallel in plan view to said base side edge, said cuffs being bonded along said base side edges to said topsheet, said free side edges in an unfolded condition, being directed inwardly of said diaper and transversely opposed to each other, and located inside transversely opposite side edges of said core so that said transversely opposite side edges are not covered with cuffs;

said cuffs being folded longitudinally along said free side edges outwardly of said diaper and being bonded at longitudinally opposite ends thereof to non-folded portions of said cuffs, wherein an outermost longitudinal edge of said free side edge is folded over the top of said free side edge and thereby is directed inward of said diaper.

2. A disposable diaper comprising:

a liquid-permeable topsheet;

a liquid-impermeable backsheet;

a liquid-absorbent core sandwiched between said topsheet and said backsheet;

said topsheet, said backsheet and said core assembled together so as to form a front zone, a rear zone and a crotch zone extending between said front zone and said rear zone;

a pair of cuffs extending longitudinally and generally parallel to each other along said front zone, said rear zone and said crotch zone;

each of said cuffs having a base side edge and an elastic free side edge extending generally parallel in plan view to said base side edge, said cuffs being bonded along said base side edges to said topsheet, said free side edges in an unfolded condition, being directed inwardly of said diaper and transversely opposed to each other, and located inside transversely opposite side edges of said core so that said transversely opposite side edges are not covered with cuffs;

said cuffs being folded longitudinally along said free side edges outwardly of said diaper and being bonded at longitudinally opposite ends thereof to non-folded portions of said cuffs;

further comprising a coversheet centrally formed with a longitudinally extending elongated opening, said coversheet being bonded at least along its outer periphery to said topsheet;

said elongated opening positioned to expose said crotch zone;

said folded free side edges of said cuffs positioned in said crotch zone being exposed in said elongated opening.

* * * * *